United States Patent
Haberland et al.

(10) Patent No.: US 9,322,760 B2
(45) Date of Patent: Apr. 26, 2016

(54) CONTACT ANGLE MEASURING INSTRUMENT

(71) Applicant: SITA Messtechnik GmbH, Dresden (DE)

(72) Inventors: Ralf Haberland, Dresden (DE); Lukas Pescoller, Bruneck (IT); Sebastian Gottschall, Dresden (DE); Lars Schümann, Dresden (DE)

(73) Assignee: SITA Messtechnik GmbH, Dresden (DE)

( * ) Notice: Subject to any disclaimer, the term of this patent is extended or adjusted under 35 U.S.C. 154(b) by 0 days.

(21) Appl. No.: 14/738,978

(22) Filed: Jun. 15, 2015

(65) Prior Publication Data
US 2015/0362417 A1    Dec. 17, 2015

(30) Foreign Application Priority Data
Jun. 13, 2014   (DE) .................. 10 2014 211 369

(51) Int. Cl.
| | | |
|---|---|---|
| *G01C 1/00* | (2006.01) | |
| *G01B 1/00* | (2006.01) | |
| *H04N 7/18* | (2006.01) | |
| *G01N 13/02* | (2006.01) | |
| *G01B 11/26* | (2006.01) | |

(52) U.S. Cl.
CPC .............. *G01N 13/02* (2013.01); *G01B 11/26* (2013.01); *G01N 2013/0208* (2013.01)

(58) Field of Classification Search
CPC .......... G01N 13/02; G01N 2013/0208; G01N 2013/0241; A61F 2/2472; A61F 2002/7635; G01B 11/02; G01L 1/24; H04N 7/18

USPC ........... 356/154, 138, 150; 348/135, E07.085
See application file for complete search history.

(56) References Cited

U.S. PATENT DOCUMENTS

| | | | | |
|---|---|---|---|---|
| 4,688,938 A | * | 8/1987 | Demoulin ............... | G01N 13/02 356/138 |
| 5,268,733 A | | 12/1993 | Wright et al. | |
| 2002/0135581 A1 | | 9/2002 | Russel et al. | |
| 2009/0180106 A1 | * | 7/2009 | Friedrich ............... | G01N 13/02 356/138 |

FOREIGN PATENT DOCUMENTS

| | | |
|---|---|---|
| DE | 4302400 A1 | 8/1994 |
| DE | 19754765 C1 | 7/1999 |
| DE | 10214439 A1 | 2/2004 |
| DE | 102005043753 A1 | 3/2007 |
| EP | 1729109 A1 | 12/2006 |
| JP | 2009036634 A | 2/2009 |
| WO | 0122058 A1 | 3/2001 |

* cited by examiner

*Primary Examiner* — Hoa Q. Pham
*Assistant Examiner* — Sunghee Y Gray
(74) *Attorney, Agent, or Firm* — Michael Soderman

(57) ABSTRACT

The subject matter of this invention is a device for measuring the contact angle of a liquid drop on a material surface. The shadow of a drop of a test liquid is projected onto a tilted shadow surface. An image of the drop on the shadow surface is recorded with an image recording device, and the contact angle is calculated from the image and the known angle of tilt of the shadow surface. A method that is suitable for this is likewise disclosed.

11 Claims, 3 Drawing Sheets

CONTACT ANGLE MEASURING INSTRUMENT

CROSS-REFERENCE TO RELATED APPLICATIONS

This application is claims the benefit under 35 USC 119 of German Application No. DE 10 2014 211 369.5 filed on Jun. 13, 2014; this application is incorporated by reference herein in its entirety.

BACKGROUND

The subject matter of the instant invention is a device and a method for measuring the contact angle of liquid droplets on material surfaces.

The wetting capability of surfaces of metal and plastic parts is an important quality characteristic before subsequent process steps such as coating or gluing. Inadequate wetting capability of the metal and plastic surfaces leads to a loss of quality, so the required functionality is no longer ensured. The causes can be impurities and insufficient surface energy of the parts. In the case of metal parts, the contamination of the surface can be evaluated with a cleanliness check via fluorometry. The fluorometry technique is not suitable for a cleanliness check of plastic surfaces, though, because they usually have a high level of autofluorescence. A cleanliness check of the plastic surfaces can be done through the wetting check under certain circumstances. A good wetting capability is achieved when the surface energy of the part is greater than the surface tension of the coating material. The surface energy of ideal clean parts can be specifically increased or changed with surface pretreatment, for instance with a plasma treatment or by coating them with special functional layers. The desired effect of this pretreatment is to be checked on a regular basis within the framework of the quality assurance, in order to ensure a high level of process reliability.

The state of the art with regard to a simple check of the wetting capability of the surfaces currently involves the use of test inks. The test-ink method is a quick check that provides the user with an approximate value for the surface energy of the part to be checked. In the process, test liquids with a defined surface tension are applied to the part to be checked. If the surface energy of the metal or plastic part is greater than the surface tension of the test ink, the applied ink spreads out. In the reverse case, when there is a greater surface tension of the test ink, the test liquid contracts and irregular droplets are formed. This method can only be used in a limited way because the maximum surface energy of the test specimen that can checked is limited to 72 mN/m by the largest possible surface tension of a test ink. Furthermore, the following drawbacks arise when the test inks are used to check the wetting:

The test inks are applied in a two-dimensional fashion, making the surfaces to be examined very dirty.
The chemicals used in the test inks are poisonous and reprotoxic in part. Special precautions are to be taken during use and disposal.
Test inks only have a limited shelf life.
Test-ink series of different liquid mixtures are not comparable due to different inter-molecular interactions.

Measurement of the contact angle of a liquid on the solid is a further possibility for checking the wetting capability of metal and plastic surfaces. The contact angle measuring instruments currently offered on the market are based for the most part on the sessile drop method. This involves the evaluation of the drop contour of a liquid drop that is previously put in place by taking a shadow image with the aid of image processing. The surface energy of the solid can be precisely determined via the contact angle with this method. The commercial measuring instruments based on this method involve in principle a two-part structure. The measurement module is comprised of a proportioning unit for applying a liquid drop with a specific volume to the surface and an optical system made up of a camera with an objective lens and lighting. The optical axis is aligned in parallel with the surface of the solid. The shadow image that is generated in that way is recorded and transferred to a connected PC. Software determines the drop contour and the contact angle from the shadow image and then calculates the surface energy. There are mobile contact angle measuring instruments as well as stationary laboratory measuring instruments. Well known suppliers are, for example, the company Krüss with the measuring instrument GH11, the company DataPhysics with the measuring instrument PCA 100M, the company Fibro System AB with the measuring instrument PGX and the company Sindatek with the measuring instrument Sindatek 100P. The drawbacks of these contact angle measuring instruments are the high price,
the large contact surface that is required (surfaces with complex geometries cannot be checked),
the very low level of automation (user intervention is necessary) and
the limited mobility in the process check because of the required use of a PC.

An instrument for determining the concentration of a material in a solution influencing the contact angle is described in EP 1 729 109 A1. Two cameras are used here that record the contact angle of a solution droplet on the material surface at right angles to one another.

A similar, less automated approach is described in U.S. Pat. No. 5,268,733. The shadow of the drop is projected onto a surface perpendicular to the material surface here via a light source that emits light in parallel with the material surface. This surface has a scale, so the contact angle can be directly read on the surface. This structure obviously involves a solution that can only be used for laboratory measurements. As can be seen, a complex adjustment of the specimen surface is necessary vis-a-vis the scaled shadow surface. Industrial use requires, however, a quick measurement with robust designs.

A further drawback of the known contact angle measuring instruments that are based on the principle of EP 1 729 109 A1 is that the material surface tends towards mirroring under certain circumstances. Because of that, it is difficult for the evaluation software that is used to correctly determine the course of the material surface. Faulty calculations could come about that can only be recognized and corrected with a human follow-up at present.

DE 197 54 765 C1 describes a contact angle measuring instrument in which a drop of test liquid is set down on a surface. This drop is illuminated with a light beam running in parallel with the surface that is redirected by a prism. The light is redirected by a second prism into a camera after passing through the drop. The digitalization and, after that, the calculation of the contact angle take place in the camera. Recording the contact angle with sufficient precision is difficult with this design, because it is naturally directly formed on the surface and has to be captured by the second redirecting prism in its contact with the surface. If damage to the edge of the prism or dirt exists here, a precise measurement is hardly possible.

SUMMARY

The subject matter of this invention is a device for measuring the contact angle of a liquid drop on a material surface.

The shadow of a drop of a test liquid is projected onto a tilted shadow surface. An image of the drop on the shadow surface is recorded with an image recording device, and the contact angle is calculated from the image and the known angle of tilt of the shadow surface. A method that is suitable for this is likewise disclosed.

DETAILED DESCRIPTION

The task arises of proposing a contact angle measuring instrument that also has a solution to the problem of the recognition of the position of the surface by the software in addition to that of industrial use.

The problem is solved as per the invention with an arrangement according to claim 1. The method as per the invention is disclosed in claim 9. Advantageous embodiments are described in the dependent sub-claims.

The arrangement as per the invention has a lighting device, an image recording device, a shadow surface and a drop dispenser; the lighting device generates a light beam in parallel with a material surface. A drop of sample liquid is applied to the material surface with the aid of the drop dispenser. The light beam projects a silhouette of the drop on the shadow surface. It is important for the invention that the shadow surface is tilted vis-a-vis the material surface at an angle less than 90° and greater than 0.5°, preferably between 45° and 5°, and as an especial preference between 10° and 30°. The image that arises on the shadow surface is recorded and digitized via the image recording device. This image can be saved. As a preference, the image is subjected to further processing, and the contact angle is determined and output and/or recorded, in a data-processing device integrated into a device as per the invention or connected with it.

The lighting device generates the light beam that is in parallel with the material surface to the extent possible either by having a light source emit it in a direction directly parallel to the material surface or by having a corresponding light beam redirected. White light is preferred. It could, however, also be advantageous to select monochromatic light, for instance if the sample liquid absorbs certain wavelengths especially well or if the shadow surface is suitable for reflecting certain wavelengths well or reacting to them with fluorescence. As a preference the beam divergence is less than 15°, as a special preference less than 5° and as a very special preference less than 3°. Preferred embodiments provide for a laser diode emitting in parallel with the material surface or a light-emitting diode with an appropriate lens system for beam parallelization here. Preferred embodiments that involve redirection have a light source (for instance a light-emitting diode or a halogen lamp) whose light is parallelized to a great extent with suitable measures such as an arrangement of lenses and/or apertures and subsequently aligned in parallel with the material surface via the redirection device. Mirrors or prisms, as an example, are suitable to be redirection devices. In addition, measures for beam shaping (apertures and lenses) can also be used. A further preferred embodiment provides for a bundle of optical fibers (fiber array) as a redirection device that leads the light generated at a suitable place in the device as per the invention to the emission location and emits it there in parallel with the material surface. The collimating effect of the optical fibers can be used in an advantageous way for beam parallelization here. Combined solutions that, for example, feed the light via a bundle of optical fibers to a mirror or a prism are also preferred.

Contrary to the solutions from the state of the art that provide for an arrangement of shadow surfaces that are perpendicular to the material surface to the extent possible in order to avoid a distortion of the shadow image, the shadow surface of the device as per the invention is tilted at an angle deviating by 90° from it. The shadow surface is tilted vis-a-vis the material surface to the effect that the base line of the shadow surface on the material surface runs in a perpendicular fashion to the optical axis of the parallel light beam and is closer to the drop than the rest of the shadow surface. The base line is understood to mean the line at which the lower edge of the preferably rectangular shadow surface meets the material surface. A symmetrical, especially a long drawn-out image of the drop that is distorted at the height of the drop arises on the shadow surface. This is advantageous because the area on the contact location between the material surface and the drop that is especially of interest is likewise distorted and enlarged in that way. In contrast, the lateral dimensions of the drop shadow that are perpendicular to the optical axis of the parallel light beam are not distorted. The actual shape of the drop and, in particular, the contact angle can be calculated according to simple geometric laws from the image of the drop on the shadow surface and the knowledge of the angle of tilt of the shadow surface.

These calculation possibilities are explained in FIGS. 2 to 4. The length of the shadow (17) is independent to a great extent from the distance of the drop (7) to the shadow surface (8) and is essentially only dependent upon the height of the drop (7) and the angle of tilt α of the shadow surface (8) to the surface (3) of the sample body (12) (material surface). The length of the shadow Z' is greater than or equal to the height Z of the drop (7). The actual height of each point of the drop edge (as a section through the drop (7) at its highest point perpendicular to the optical axis of the parallel light beam) can be determined from the relationship:

$$Z = Z' * \sin(\alpha)$$

wherein Z is the actual height of the drop point, Z' is the distance of the shadow point from the base line of the shadow surface (8) and α is the angle of tilt of the shadow surface (8).

It is bright, preferably white, in order to make a clearly identifiable image of the drop shadow on the shadow surface (8) possible. Another preferred embodiment is supplied with a fluorescent coating that especially reacts with fluorescence to the light wavelength or wavelengths used by the lighting device. This leads in an advantageous way to a stronger contrast between the shadow image of the drop and the illuminated areas of the shadow surface (8).

The image recording device is preferably arranged in front of the shadow surface in such a way that its optical axis is perpendicular to the shadow surface. As a preference, the deviation from this perpendicular alignment is less than 30°, with a special preference for being less than 15° and with a very special preference less than 5°. A camera or digital camera is preferably used as the image recording device. In a further preferred embodiment, there is a fiber-optic array instead of a camera that records the image of the shadow surface and passes it along to a camera, a CCD array or another type of image recording apparatus at a different location.

The sample dispenser corresponds in its design to the solutions known from the state of the art. It preferably has a storage tank, a needle with a cannula and a proportioning unit. To put a drop on the material surface, the drop dispenser or at least its needle is lowered so far that the needle tip is very close (approx. 0.2 to 1 mm apart) to the material surface. The proportioning unit discharges a defined quantity of liquid from the storage container and feeds it to the needle, which puts the drop forming at its end on the material surface. The quantity of liquid that is actually metered out depends on the viscosity of the liquid, the temperature and the measurement task and has to be correspondingly adjusted. The lowering of the needle can be controlled in a manual fashion or via an automatic control unit. As a preference, the quantity of liquid for the drop formation is metered out in an automatic fashion. As a very special preference, an automatic data-processing system takes over this control, so the environmental parameters (temperature) can be included in the control process. In a preferred embodiment, the proportioning unit has further sensors, in particular distance sensors for determining the distance of the needle tip to the material surface. The measured values of these sensors are preferably also processed in the automatic control unit. As a special preference, this data-processing system is identical with the one that is also used to evaluate the shadow recording.

In a preferred embodiment, the device as per the invention has more than one drop dispenser; each drop dispenser can advantageously apply a different test liquid to the material surface.

In a further preferred embodiment, a nozzle is used as the drop dispenser.

The device as per the invention is preferably designed to be a manual device that can be moved by hand (or an automatically handled device with similar dimensions). The device advantageously combines both the proportioning unit and the lighting device, the shadow surface and the image recording device in one housing. In a simple embodiment, the control data and measured data are transmitted in a wireless or wired fashion (e.g. via optical fiber) to one or more data-processing devices. As a special preference, the data-processing device is likewise integrated into the device as per the invention. Selected control parameters and measured values are optionally transmitted to external data-processing or presentation devices (wireless or wired). It is possible in a particularly advantageous way to set the device down on the material surface to apply the drop and carry out the measurement. It is thereby possible to measure curved surfaces or surfaces of parts that cannot be transported into a laboratory environment. In the case of curved surfaces, it is to be noted that the curvature is not permitted to be so strong that the measurement distortion because of the lifting or lowering of the drop in the parallel light beam due to the curvature leads to measurement errors outside of the strived-for tolerance. The light beam that runs parallel to the material surface and that projects the shadow image of the drop onto the shadow surface is to be regarded in this sense in the case of curved surfaces as being parallel to the material surface when it is in the contact point of the drop in parallel with a tangential plane in this contact point. It is especially advantageous when the side of the device that is set down on the material surface has a defined design; as a special preference, it is flat and smooth for this or at least has a minimum of three defined contact points. After the setdown, a surface line is repeatably defined that is known during the processing of the measured values or can be specified in the programming of the data-processing device. There are consequently no problems with the identification of the material surface as they are known in the prior art.

The shadow surface has to have a defined base line for a measurement that is precise as possible. It is therefore preferably beveled or ground in the area of contact with the material surface so that there is no stepping, or as little stepping as possible, of the material surface to the shadow surface. The shadow surface is preferably designed in the form of an exchangeable component, because it is expected that it will be damaged after a series of measurements, especially in the area of the base line. As a preference, the shadow surface will preferably only be held in a force lock in guide grooves between two lateral areas. The lateral areas likewise close up at the height of the base line, so the corners of the shadow surface are protected. In a further preferred embodiment, the shadow surface is contained in a module that can be inserted into the device. Different angles of tilt of the shadow surface are possible because of that via an exchange of the modules in connection with the adjustability of the angle of the image recording device over the shadow area.

An especially preferred embodiment of the contact angle measuring instrument as per the invention is shown in a schematic diagram in FIG. 1. The drop (7) is illuminated with a light source e.g. an LED (4). This takes place through an optical axis (A) at a steep angle (e.g. 70°) to the surface (3). The light is redirected along the optical axis (B) that is horizontal or parallel to the surface (3) in a first redirection device (6) (e.g. a prism or mirror). The drop throws a shadow onto the shadow surface (8), which is arranged with a flat tilt (e.g. $\alpha=25°$) vis-a-vis the surface (3). A camera (1) records an image of the shadow of the drop (7) on the shadow surface (8) via an objective lens (2) (lens) through the optical axis (C-D) that is arranged at a steep angle, preferably perpendicular, vis-a-vis the shadow surface (8). The direct incidence of light outside of the optical axes (A-B-C-D) from the lighting (4) is prevented via a separation (5) with a slit aperture (13) open towards the surface (3) with an opening the size of the drop dimension (e.g. drop height Z*drop width X=1.2 mm*6 mm), so only light that is nearly parallel is thrown onto the drop. The drop (7) is applied via a proportioning needle (9) on the surface (3) that can be lowered by means of a lowering device (14). The quantity of sample liquid to form an individual drop (e.g. 1 microliter) is specified by a proportioning device e.g. a pump (10) with a connected liquid tank (11). The lighting (4), the lowering device (14) and the proportioning device (10) are preferably controlled by a microprocessor (15). The camera (1) can optionally be controlled by the microprocessor or by an externally connected computer. The image processing and the calculation of the contact angle and of the volume of the drop are carried out by the microprocessor (15) or a connected computer. The measurement results are shown on a display of the device or on a connected computer. A narrow-band LED with a small beam angle (e.g. 10°) and with a wavelength $\lambda$ that has a maximum level of absorption by the sample liquid is preferably selected for the light source (4). One or more slit apertures (16) can be used for the parallelization of the light in the optical channel (A).

The method as per the invention provides for the following measurement sequence:

The light source of the lighting device is switched on, and the device is positioned on the material surface.

A null image of the shadow surface without a shadow is recorded and saved.

The drop is formed on the proportioning needle, and the proportioning needle is lowered towards the surface to a distance of around 0.4 mm (dependent upon the type of sample liquid); the drop is put on the surface because of that.

The proportioning needle is moved back into the starting position.

An image of the shadow is recorded and offset against the null image to form a differential image (resulting image); dirt and brightness variations on the shadow surface itself are eliminated.

The process for determining the actual drop parameters from the differential image is carried out as follows (see FIG. 4):

The upper edge of the shadow of the drop is determined in the resulting image, and it provides a point sequence p (X, Z').

The closest circle K(mx, mz, r) with (mx, mz) as the center point and r as the radius that has the minimum quadratic distance to the points P(X, Z'*sin(α)) with α=the angle of the shadow surface (8) to the surface (3) can now be determined by means of a circle equalization.

The drop height h results from h=r+mz. With a contact angle of φ<90°, mz is negative because mn lies below the surface (P) in that case. With a contact angle of φ>90°, mz is positive because mz lies above the surface (Q) in that case.

The drop width follows as a chord with Z=0.

The contact angle φ results from the slope of the tangent at the points of intersection of the chord with the circle.

The volume of the drop follows from V=h²*(PI/3)*(3*r−h).

DETAILED DESCRIPTION OF THE PREFERRED EMBODIMENTS

Design Example

Figure 1:
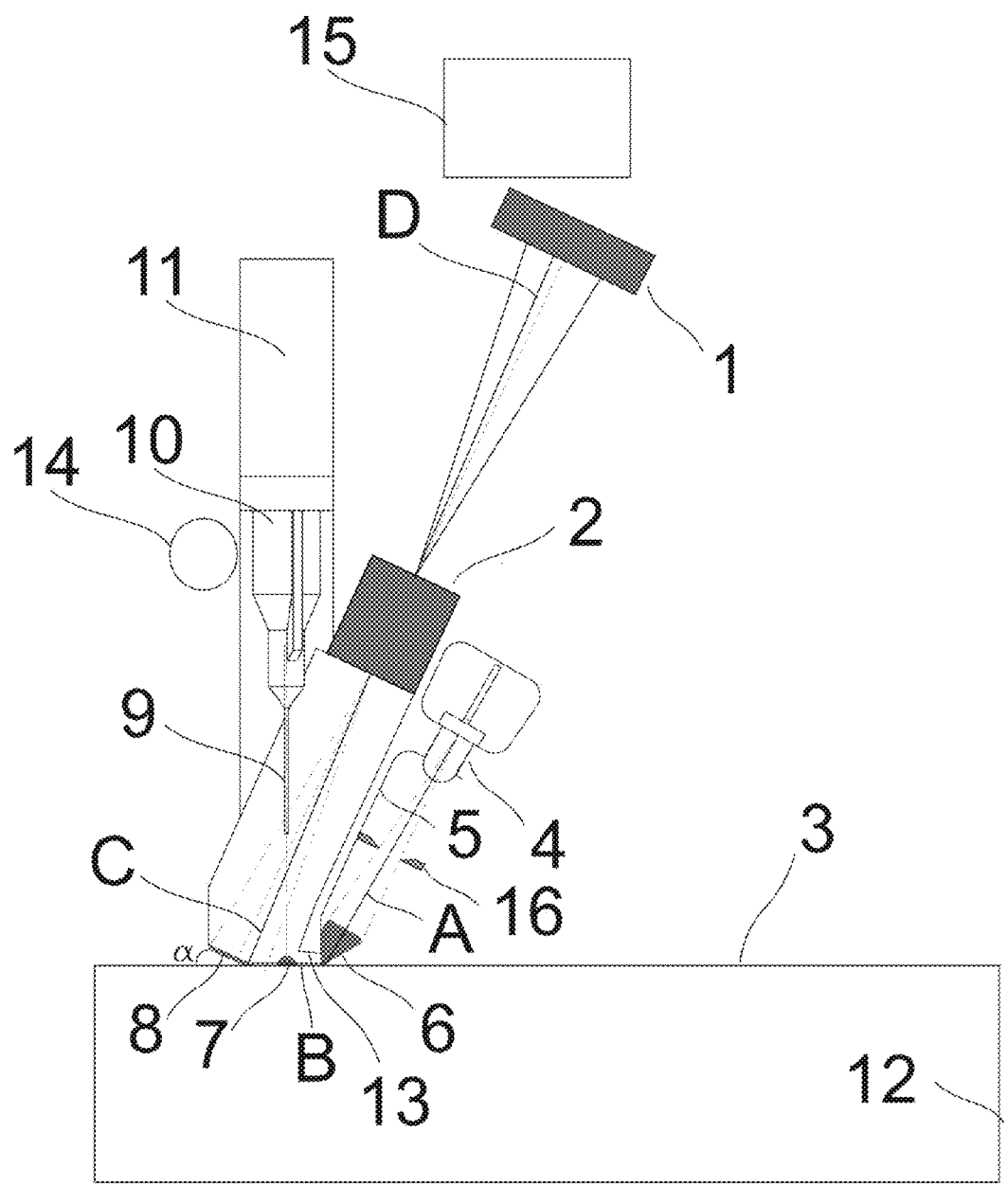
FIG. 1 shows the basic structure of a preferred embodiment of the contact angle measuring device as per the invention.
Figure 2:
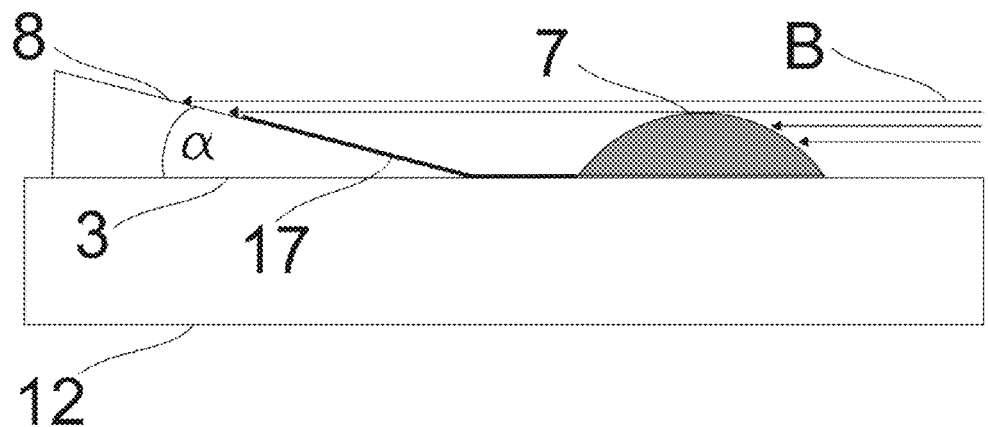
FIG. 2 shows a schematic diagram of the imaging circumstances of the drop onto the tilted shadow surface.
Figure 3:
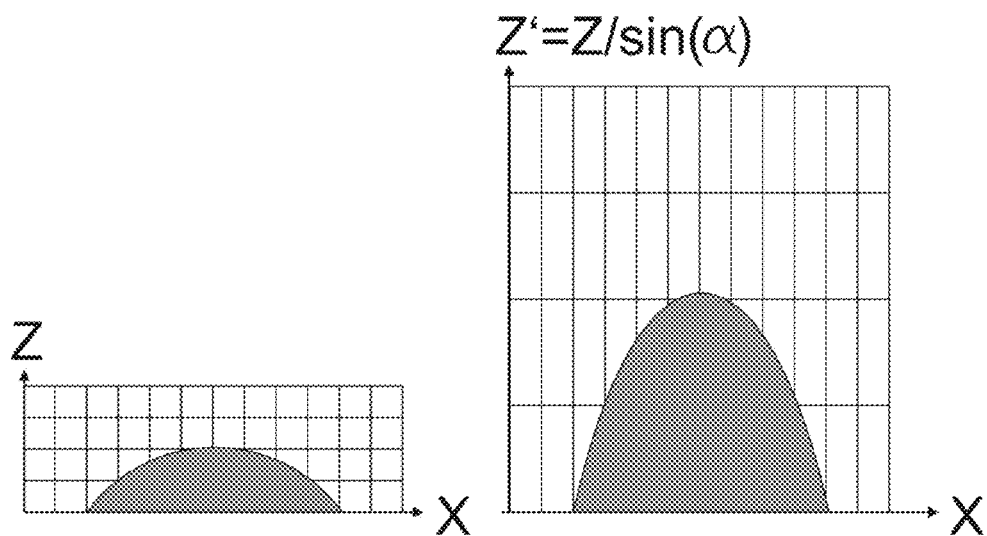
FIG. 3 compares the imaging circumstances of the drop shadow in the case of a vertical shadow surface (left-hand side) and a tilted shadow surface (right-hand side).
Figure 4:
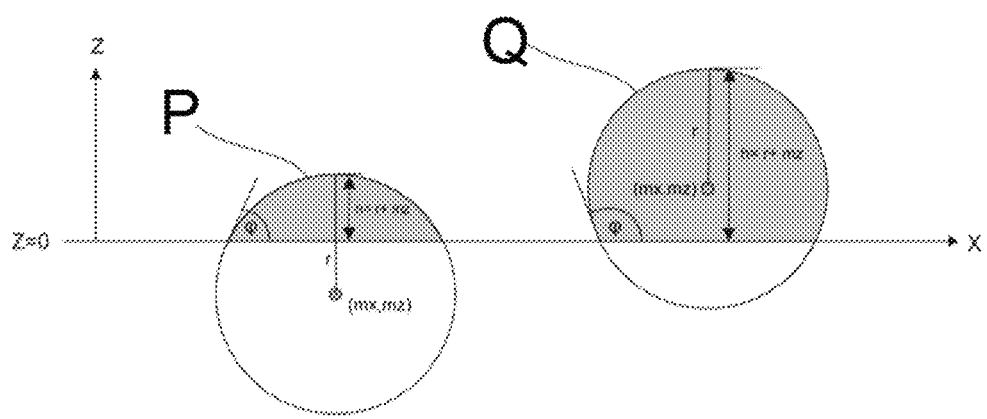
FIG. 4 shows the geometric conditions for determining the drop parameters for heavily wetting liquids (left-hand side, drop P) and partially wetting liquids (right-hand side, drop Q) on a surface.

The contact angle measuring instrument is arranged in a housing and has a display and operating keys in addition to the sensor device. The measured values can be read from the display. Furthermore, there is an evaluation and storage unit (15), as well as a USB interface to transfer the measured values that are stored to a computer and an electrical power connection. The contact angle measuring instrument is directly set down on the surface (3) to be investigated.

A drop (7) with a volume of approx. 1 µl is set down on the surface (3) of the sample body (12) via the proportioning needle (9) (internal diameter of the needle: 0.15 mm, length ½") by means of the proportioning device (10). The tank (11) of the proportioning device (10) has a total volume of 10 ml from which the drop volume is drawn by means of a miniaturized piezoelectric diaphragm pump. The proportioning needle (9) is moved via a miniature linear motor as the lowering device (14). The evaluation and storage unit (15) likewise provides control. Demineralized water (demineralized or distilled water) serves as the test fluid.

The lighting is realized by an LED (4) that emits white light. The beam diameter is 3 mm with a beam expansion of 10°. The light beam (optical axis A) is emitted from the LED at an angle of 70° to the surface to be investigated. The light (A) is redirected in parallel with the surface (3) (beam (B)) by means of a prism (6) made of transparent plastic.

The light beam (optical axis B) passes through the drop (7) and reaches the shadow surface (8). It is made of aluminum and tilted at an angle (α) of 25° to the material surface (3). The shadow surface (8) has a width of 5 mm, with a length of 14 mm, on the edge touching the material surface (3).

The shadow of the drop is depicted in a distorted fashion in accordance with the tilt of the shadow surface (8) on the shadow surface (8).

The multi-lens optical system (f=16 mm) of the objective lens (2) is perpendicular to the shadow surface (8) and has an objective spacing of 32 mm to it. The objective lens (2) records the image on the shadow surface (8) (optical axis C). The camera (1), which records the image captured by the objective lens (2), follows behind the objective lens (2), likewise with a spacing of 32 mm (optical axis D). The camera (1) is designed to be a CCD camera and has a resolution of 1280×1024 pixels.

The image in the form of a digital signal sequence is transferred from the CCD camera to the evaluation unit (15) and further processed, stored and, if applicable, transferred on there.

As a result of the processing, the contact angle is calculated from the distorted image in accordance with the calculation methods specified further above and shown in the display as a measured value.

LIST OF REFERENCE NUMERALS

1 Camera
2 Objective lens
3 Surface
4 Light source
5 Separation
6 First redirection device
7 Drop
8 Shadow surface
9 Proportioning needle
10 Proportioning device
11 Liquid tank
12 Sample body
13 Slit aperture
14 Lowering device
15 Microprocessor
16 Slit aperture
A Optical axis of the lighting beam from the light source to the first redirection device
B Optical axis from the first redirection device to the shadow surface
C Optical axis from the shadow surface to the objective lens
D Optical axis from the objective lens to the camera
P Drop on a heavily wetting surface
Q Drop on a partially wetting surface

The invention claimed is:

1. Device for measuring the contact angle of a liquid drop on a material surface, having a lighting device, an image recording device, a shadow surface, at least one data-processing device and at least one drop dispenser, wherein
   a. the lighting device configured to generate a light beam parallel to the material surface that reaches the shadow surface,
   b. the drop dispenser configured to apply a drop of sample liquid to the material surface, and the light beam of the lighting device projects a silhouette of the drop onto the shadow surface,
   c. the image recording device configured to record an image arising on the shadow surface,
   characterized in that
   d. the image recording device is arranged in front of the shadow surface in such a way that its optical axis deviates less than 30° from a perpendicular position with respect to the shadow surface,
e. the shadow surface is tilted at an angle less than 90° and greater than 0.5° with respect to the material surface, and
f. the data-processing device configured to evaluate the measurement results of the image recording device and to calculate the contact angle from the image of the drop on the shadow surface and the knowledge of the angle of tilt of the shadow surface.

2. Device according to claim 1, characterized in that the lighting device generates the parallel light beam without redirection.

3. Device according to claim 1, characterized in that the lighting device generates the parallel light beam by forming the light beam of a light source and redirecting it with a mirror or prism.

4. Device according to claim 1, characterized in that the light of a light source is fed into one end of a bundle of optical fibers and the other end of the bundle of optical fibers is aligned in such a way that the emitted light generates the parallel light beam.

5. Device according to claim 1, characterized in that the shadow surface has a bright, preferably white, surface coating.

6. Device according to claim 1, characterized in that the shadow surface has a surface coating that reacts with fluorescence with the light that is emitted from the lighting device.

7. Device according to claim 1, characterized in that the image recording device is arranged in front of the shadow surface in such a way that the optical axis is on a perpendicular line to the shadow surface.

8. Device according to claim 1, characterized in that the shadow surface is beveled at its base line to the effect that it does not form a transition step from the material surface to the shadow surface.

9. Device according to claim 1, characterized in that the at least one data-processing device is also designed to control the drop dispenser, the lighting device and the image recording device.

10. Method for determining the contact angle of a liquid drop on a material surface, comprising the following steps:
a. positioning the device for measuring the contact angle on the material surface and switching on the light source of the lighting device, wherein the device is positioned on the material surface in such a way that the lighting device generates a light beam parallel to the material surface,
b. recording and saving a null image of the illuminated shadow surface without a drop shadow that is tilted at an angle less than 90° and greater than 0.5° with respect to the material surface,
c. forming the drop on the tip of the proportioning needle, lowering the proportioning needle to the proximity of the material surface and putting down the drop on the material surface,
d. moving the proportioning needle back to the starting position,
e. recording an image of the shadow of the drop on the shadow surface via the image recording device, wherein the image recording device is arranged in front of the shadow surface in such a way that its optical axis deviates less than 30° from the perpendicular line onto the shadow surface,
f. offsetting the image of the shadow of the drop with the null image to form a resulting differential image,
g. determining the drop dimensions including the contact angle from the knowledge of the tilt of the shadow surface and the dimensions of the drop shadow in the differential image.

11. Method according to claim 10, characterized in that the formation of the drop on the proportioning needle and the lowering of the proportioning needle or of the entire drop dispenser are controlled by the data-processing device.

* * * * *